United States Patent [19]

Bilbrey

[11] Patent Number: 5,290,547
[45] Date of Patent: Mar. 1, 1994

[54] MACROEMULSION HAVING AN ODOR-COUNTERACTING DISCONTINUOUS PHASE

[75] Inventor: James M. Bilbrey, Dayton, Ohio

[73] Assignee: Ronald T. Dodge Co., Dayton, Ohio

[21] Appl. No.: 870,791

[22] Filed: Apr. 16, 1992

Related U.S. Application Data

[63] Continuation of Ser. No. 606,559, Oct. 31, 1990, abandoned.

[51] Int. Cl.$^5$ .............................................. A61L 11/00
[52] U.S. Cl. ..................................... 424/76.6; 422/5; 119/171; 514/937
[58] Field of Search ............... 424/76.6, 401; 514/937; 119/171

[56] References Cited

U.S. PATENT DOCUMENTS

| | | | |
|---|---|---|---|
| 4,407,231 | 10/1983 | Colborn et al. | 424/76.6 |
| 4,816,220 | 3/1989 | Roychowdhury | 424/76.6 |
| 4,959,207 | 9/1990 | Ueda et al. | 424/76.6 |

OTHER PUBLICATIONS

Gennaro, A. R. (1985) Renington's Pharmaceutical Sciences, Mack Pub., p. 68.

Primary Examiner—Paul R. Michl
Assistant Examiner—Raj Bawa
Attorney, Agent, or Firm—Donald P. Gillette

[57] ABSTRACT

A macroemulsion composition for controlling odors and including droplets of water-immiscible, odor counteracting material dispersed as the discontinuous phase of the macroemulsion in a water soluble binder, which constitutes the continuous phase of the macroemulsion. Upon deposition of the composition onto an appropriate substrate, such as pet litter, and after evaporation of the water within the binder solution, the water soluble binder solidifies on the substrate. In so doing, the solidified water soluble binder substantially encloses the droplets of the odor counteracting material. The water soluble binder easily dissolves upon contact with water in pet excreta, thereby releasing the odor counteracting material in an amount appropriate to counteract the offensive odors at the offensive area where such counteraction is needed most.

27 Claims, No Drawings

MACROEMULSION HAVING AN ODOR-COUNTERACTING DISCONTINUOUS PHASE

This is a continuation of application Ser. No. 606,559, filed Oct. 31, 1990, now abandoned.

BACKGROUND OF THE INVENTION

This invention relates to an odor counteractant to be applied as a coating on a substrate to control or modify odors resulting from the use of the substrate in contact with malodorous material and moisture. The invention further relates to the method of forming and using a macroemulsion incorporating the counteractant and to a product comprising the macroemulsion. In particular, the invention relates to the control of odors associated with the use of pet litter.

In the past, attempts have been made to control the odor in particulate pet litter by spraying an odor-modifying material directly on the litter. The odor-modifying material gave off its own odor, which was more pleasing than the odor resulting from normal use of the litter by pets, but the effect of the odor-modifying material dissipated rather soon.

An improved odor-modifying material described by Colborn et al. in U.S. Pat. No 4,407,231 was produced by encapsulating fragrance oil as an odor counteractant in microcapsules and spraying those microcapsules on the particles of litter. The microcapsules were frangible, and the typical digging or scratching action indulged in by the pet, especially a cat, using the litter broke some of the microcapsules with each use, releasing some of the fragrance to counteract the unpleasant odors resulting from pet excreta. This same frangibility required in a certain amount of microscapsule breakage in handling and transportation of the containers of treated litter, which was not altogether bad, because it released a small amount of the fragrance, which would be sensed by the pet owner when opening the container of litter.

However, in actual use, it is desirable to have no further odor counteractant released until the pet uses it. When that does happen, it is not only essential that some of the microcapsules be broken, but it is further desirable that the amount of odor counteractant released be generally proportional to the need, which means generally proportional to the quantity of excreta rather than to microscapsule breakage. Breakage by mechanical scratching action is proportional to the activity of the animal and not necessarily to the amount of malodorous material that needs to be counteracted.

This further requires that the odor counteractant be carried by material that is soluble in pet urine to release the counteractant, whether the pet paws the litter intensely or little or not at all. Microcapsules, as used heretofore, are not very soluble and, thus, the fragrance oils contained in them are not released in proportion to need as specifically as is desired.

OBJECTS AND SUMMARY OF THE INTENTION

It is an object of this invention to provide an odor counteractant in a form that is easily applied to a substrate and is efficiently activated by moisture and by mechanical action in use.

Another object is to provide an efficient odor counteractant that is less expensive to produce than the microcapsules containing fragrance oils.

Still another object is to produce a coating material that includes an odor counteractant and is to be used on particulate pet litter to be released for odor control in proposition to the amount of excreta from the pet.

A further object is to provide a simple method of producing an odor counteractant having the foregoing characteristics.

Further objects will be apparent, after reading the following description, to those skilled in the art.

In accordance with this invention, an odor counteractant to be applied to a substrate for the control of odors is formed of viscous fragrance, or aromatic oil material, dispersed in high concentration as a long-lasting oil-in-water emulsion in water-based solution of a highly water-soluble substance capable of drying to a rigid form with droplets of the suspended odor counteractant remaining dispersed individually therein.

The mixture can be applied to a substrate and given time for the water to evaporate in order to produce, on the substrate, a dry coating with the oil droplets contained therein. When moisture is brought into contact with the coating, such as by the deposit of pet excreta thereon, the moisture will dissolve the water-soluble substance, thereby releasing the fragrance oil to perform the desired function of modifying or overcoming or counteracting the odors that are either in the excreta as deposited or are generated therein over time by bacterial action.

The fragrance oil can be brought to a high viscosity by the addition of a suitable oil-soluble thickening agent so that, when dispersed, it will not tend to coalesce and will form droplets of the proper size to be easily opened by mechanical fracturing of the dried material. I have found a number of suitable thickening agents that can be used to produce satisfactory results, but, at the present time, the most satisfactory one, from the point of view of the small quantity required and the low cost, is a polymer, (polyvinyl butyral), referred to hereinafter as PVB.

There are also a number of suitable, water-soluble substances that can form aqueous solutions in which fragrance oils can be satisfactorily dispersed, and which will continue to encase the oil droplets after the water has evaporated from the solution. Gum tahla is especially suitable to form a water-based carrier solution as a continuous phase of an emulsion in which droplets of the thickened fragrance oil can be suspended. When the emulsion has been applied to a substrate and the water competent of the emulsion is evaporated, gum tahla, with the individual fragrance oil droplets still dispersed in it, dries to a glassy-hard, but frangible state and is still very easily dissolved in moisture. The hardened gum tahla encases the droplets, which are directly embedded in it without any intervening shell, as a microencapsulated droplet would have.

DETAILED DESCRIPTION OF A PREFERRED EMBODIMENT

Fragrance oils of various kinds are well known for their ability to modify odors in their vicinity, either by masking the undesired odor or overriding it or counteracting it by chemical action. In order to keep fragrance oil from escaping into the air after the oil has been applied to a substrate, this invention divides the oil into fine droplets and disperses the droplets in a carrier liquid with which the oil is immiscible, thereby forming an oil-in-water emulsion. The carrier liquid, or at least one of its components, solidifies with the oil droplets embedded in it after being applied to a substrate. The fragrance oil can later be released by dissolving the solidified material or by breaking the solidified material along surfaces of fracture that intersect droplets of fragrance oil embedded therein. This requires that the embedding material be frangible to at least some degree, as well as being soluble in water. When the suspension is applied to particulate material, such as pet litter, it is also desirable that the solidified material not be so sticky as to cause the particulate to join together in a large lump.

The oil can be dispersed in the immiscible carrier liquid by agitating a mixture of the two to form an oil-in-water emulsion, after which the emulsion can be applied as a coating material to a substrate, such as particulate material forming a pet litter, by being sprayed thereon. It is desirable that the coating material contain a high percentage of solids, or, more specifically, a high percentage of material—primarily the fragrance oil—that is insoluble in the water carrier. Furthermore, for the fragrance oil droplets to be applied uniformly with other components of the emulsion, it is necessary that the emulsion not break down, as by having the oil droplets settle out or coalesce, and that the droplets not be too small. The droplets may be from 2 $\mu$ to 300 $\mu$ but are preferably on the order of about 15 to 25 $\mu$ in diameter. About 20 $\mu$ is the most desirable size in order that any fracturing of the solidified material be likely to intersect oil droplets contained therein.

These requirements can be met by causing the fragrance oil to have a relatively high viscosity, on the order of at least about 100–1000 cps., but preferably on the order of 200–500 cps. The oil, alone, may not normally have that high a viscosity but can be made more viscous by adding to it up to about 10% by weight of a thickening agent soluble in oil. There are a number of suitable thickening agents, such as PVB; hydrocarbon-soluble styrene-butadiene copolymers; hydrocarbon-soluble polyisoprene; hydrocarbon-soluble polyisobutylene; hydrocarbon-soluble polybutadiene; polystyrene; poly($\alpha$-methylstyrene); ($C_{10}$–$C_{20}$)alkyl-methylmethacrylates; ($C_{10}$–$C_{20}$) alkyl-acrylates, poly(yvinyl pyrrolidone; and ($C_{10}$–$C_{20}$) alkyl-methacrylate, either as homopolymers or copolymers. Petrolatum can also be used as the thickening agent. However, a weight of petrolatum equal to about half of the weight of the fragrance oil, is required to obtain viscosity in the 100–500 cps range.

I have found that, overall, PVB is the most satisfactory. While as much as about 10% by weight of PVB may be dissolved in the oil, I have found that only about 4–6% by weight of PVB need be mixed with a fragrance oil to cause the resulting mixture to have a viscosity in the desired range.

The PVB thickening agent can be mixed with some fragrance oils at room temperature; other oils must be heated to about 40° C. to dissolve the PVB in the fragrance oil satisfactorily. The amount of PVB required to thicken 1 Kg of a fragrance oil is typically about 44–58 g. After these ingredients have been mixed together sufficiently to dissolve the PVB in the oil, the mixture may be set aside at room temperature for any desired time until it is needed as one of the components in forming a quantity of coating material.

The other component in the coating material is an aqueous solution of a water-soluble polymer binder. The solution is used as the continuous phase of a oil-in-water emulsion in which the thickened fragrance oil is the discontinuous phase. Suitable binders include: gum tahla; gum arabic; dextrin; low-molecular weight polyvinyl alcohol having a molecular weight less than about 4000; low-molecular weight polyvinyl methylether-co-maleic anhydride (PVM/MA); and Gantrez-AN, which is supplied by GAF Corp.

Of these, gum tahla is preferred commercially at the present time due to its low cost.

While a suitable aqueous solution of a binder may consist of about 15% to about 45% gum tahla by weight, preferably at least about 30% gum tahla should be used, and it is not really economical to exceed about 40%. I have found that a particularly satisfactory solution can be made using the ratio of 320 g. of gum tahla in 680 g. of water to form a 32% solution. These ingredients can be mixed at room temperature, although the temperature can be elevated to as much as about 40° C. to speed up the dissolution of the gum tahla. After the mixing of these materials is complete, that mixture can also be set aside for an indeterminate time (with preservative added).

The coating emulsium is formed by mixing proper quantities of the thickened fragrance oil and the aqueous solution of the binder. The ratio of non-aqueous material to water should be between 25% and 60% by weight. In the case of an emulsion to be made using oil thickened by about 6% by weight of PVB, and a 32% solution of gum tahla in water, a particularly satisfactory emulsion can be made by adding the thickened oil to the gum tahla solution in the ratio of 200 g. of the thickened oil to 1 Kg. of the gum tahla solution. This is preferably done at room temperature to keep the viscosity of the oil as high as possible, since that makes the resulting emulsion more stable than if the viscosity were lower. While this can be satisfactorily done with a turbine blade stirrer revolving at about 100 –200 rpm and, in relatively small batches, can even by done by hand, it is not so much the speed or mode of agitation that is of concern as the size of the droplets of fragrance oil formed in the gum tahla solution. As previously stated, these droplets should be about 20 $\mu$. This can be monitored by examining samples of them under a microscope, although, with experience, that may become unnecessary. It is known that the discontinuous phase in an emulsion intended to last for a long time should not consist of particles that re-coalesce too soon.

The reason for not making the droplets too small may be more difficult to recognize. It is desired that any fracture of the solidified gum tahla intersect one or more of the embedded droplets, but if the droplets are too small, the fracture may bypass them, and no fragrance oil will be released. Of course, release of even very small droplets of the fragrance oil by dissolving any volume of the solidified gum tahla will be expected.

Forming the emulsion can also be assisted by adding a small quantity of a surfactant, including such surfactants as sodium lauryl sulphate or one of the Spans, e.g., sorbitan tristearate or sorbitan trioleate or sorbitan monooleate, the Span 80, which can be obtained from I.C.I. Corp., to the mixture. In forming about 1 Kg of emulsion, about 0.40 g. of sodium lauryl sulphate is ample, although its use can be avoided entirely if the main ingredients are stirred promptly. The resulting emulsion will be stable for weeks or even months. If it breaks down, it may be easily re-emulsified to the proper droplet size by being stirred.

Gum tahla, or other binder materials, will be attacked by bacteria unless such attack is prevented. To do so, I add between about 0.1% and 5% by weight of a suitable bactericide, such as Dowacil 75 to the mixture as a preservative. Other suitable bactericides may also be used, such as Kathon supplied by Rohm and Haas, and Germaben supplied by Sutten Labs. The Dowacil 75 can be added while the emulsion is being formed. The preferred amount of Dowacil 75 in the mixture is about 1.7 g. per Kg, which is sufficient to protect the gum tahla from bacterial effect that would cause the emulsion to develop an unpleasant odor in a relatively short time.

The bactericide has an additional effect; it will be available to attack any bacteria brought in by the moisture when the coating is activated by that means. Thus, unpleasant odors directly emanating from the pet excreta or other malodorous material that comes into contact with the coating of this invention will be made less odious or completely eliminated by the fragrance oil, and any odors that would arise due to bacterial action, either before or after use of the coating material, will also be held in check. As a result, the material can be described as triple-acting: it provides a pleasant odor of its own; it acts as a malodor counteractant; and its bacterial component protects the mixture before use and after use.

A small quantity of dye, typically from 0 to about 2% by weight, and preferably about 0.8%, may also be added to the ingredients of the emulsion while they are being stirred together.

The formula for the ingredients of them macroemulsion are:

| FORMULA | | |
|---|---|---|
| | Preferred Value | Range of Values |
| water | 52.2% | 40–75% |
| binder | 27.3% | 15–45% |
| oil | 16.0% | 4–25% |
| preservative | 2.2% | 0.1–5% |
| dye | 0.8% | 0–2% |
| surfactant | 0.8% | 0–2% |
| thickening agent | 0.7% | 0–10% |

The mixture, when sprayed on pet litter, dries to a hard, glassy solid. While it dissolves readily in pet urine, it is not adversely affected by humidity nor by high ambient temperature. It can be broken up by the mechanical action of a pet's scratching the litter, and that will release at least some of the 20 $\mu$ droplets of oil.

It is important that the thickness of the layer of binder, when dry, be greater than the diameter of the majority of the droplets so as to cover them. Otherwise, the droplets would not be embedded in the binder and would be exposed to the atmosphere, which would allow them to evaporate before being used to counteract an odor.

The resulting litter material is vastly superior to the prior microencapsulated material described in U.S. Pat. No. 4,407,231 because the present material dissolves so much more easily. As a result, the amount of macroemulsion required is only about half the amount of the microencapsulated material.

What is claimed is:

1. A macroemulsion that is to be applied to a substrate to solidify thereon and that comprises:

(a) from about 4% to about 25% by weight discrete droplets of odor counteractant oil immiscible with water and having a diameter between about 2 μ and 300 μ;

(b) a continuous liquid phase enveloping the discrete droplets and comprising an aqueous solution of water-soluble polymer binder, the binder having a weight between about 15% and 45% of the weight of the macroemulsion, and the water having a weight between about 40% and 75% of the weight of the macroemulsion, the droplets being suspended in the water-soluble polymer without any intervening shell; and (c) optionally, a surfactant.

2. The macroemulsion of claim 1 in which the odor counteractant comprises a solution of a polymer thickening agent in fragrance oil in which the concentration of the thickener is not greater than about 10% by weight.

3. The macroemulsion of claim 2 in which the concentration of the thickening agent is about 6% by weight.

4. The macroemulsion of claim 2 in which the thickening agent is a member of the class of polyvinyl butyral, hydrocarbon-soluble styrene-butadiene copolymers, hydrocarbon-soluble polyisoprene, hydrocarbon-soluble polyisobutylene, hydrocarbon-soluble polybutadiene, styrene, ($C_{10}$–$C_{20}$) alkyl-methacrylates, ($C_{10}$–$C_{20}$) alkyl-acrylates, poly(vinyl pyrrolidone), and ($C_{10}$–$C_{20}$) alkyl-methacrylate either as homopolymers or copolymers, and petrolatum.

5. The macroemulsion of claim 1 in which the thickening agent is polyvinyl butyral.

6. The macroemulsion of claim 1 in which between about 40% and 75% of the total weight of the macroemulsion is water.

7. The macroemulsion of claim 6 in which the weight of the water is not greater than about 53% of the total weight of the macroemulsion.

8. The macroemulsion of claim 2 in which the binder is selected from the group consisting of gum arabic, dextran, low-molecular weight polyvinyl alcohol having a molecular weight less than about 4000, and low-molecular weight polyvinyl methylether-co-maleic anhydride, and gum tahla.

9. The macroemulsion of claim 8 in which the binder is gum tahla.

10. The macroemulsion of claim 8 in which the weight of the binder is about 27.3% of the total weight of the macroemulsion.

11. The macroemulsion of claim 1 comprising a maximum of about 2% by weight of a surfactant to enhance the formation of the macroemulsion from said discrete droplets of odor counteractant oil and said aqueous solution of water-soluble polymer binder.

12. The macroemulsion of claim 11 in which the surfactant is a member of the class consisting of sodium lauryl sulphate and a Span in which the amount of surfactant is less than 0.1% of the total weight of the macroemulsion.

13. The macroemulsion of claim 1 in which the diameter of the droplets is between about 15 μ and 75 μ.

14. The macroemulsion of claim 13 in which the average diameter of the droplets is not greater than about 20 μ.

15. The macroemulsion of claim 1 comprising between about 0.1% and 5%, by weight, of preservative.

16. The macroemulsion of claim 15 in which the preservative is an antimicrobial agent comprising 69% of 1-(3-Chloroallyl)-3,5,7-triaza-1-azoniaadamantane chloride, 25% of sodium bicarbonate, and 4% of Hexamethylenetetramine hydrochloride.

17. The macroemulsion of claim 16 in which about 2.2% of the weight of the microemulsion is an antimicrobial agent comprising 69% of 1-(3-Chloroallyl)-3,5,7-triaza-1-azoniaadamantane chloride, 25% of sodium bicarbonate, and 4% of Hexamethylenetetramine hydrochloride.

18. The macroemulsion of claim 1 in which the binder is gum tahla, the thickening agent is polyvinyl butyral, and the preservative is an antimicrobial agent comprising 69% of 1-(3-Chloroallyl)-3,5,7-triaza-1-azoniaadamantane chloride, 25% of sodium bicarbonate, and 4% of Hexamethylenetetramine hydrochloride.

19. The macroemulsion of claim 18 comprising the following components in approximately the following weight percentages:

| | |
|---|---|
| water | 52.2% |
| binder | 27.3% |
| fragrance oil | 16.0% |
| preservative | 2.2% |
| surfactant | 0.8% |
| thickening agent | 0.7% |
| dye | 0.8% |

20. An odor-counteracting medium comprising:
 (a) a substrate; and
 (b) a dried film adhered to the substrate, said dried film comprising:
  (i) about 44% to about 92% by weight of a water-soluble, frangible, polymeric binder, and
  (ii) about 8% to about 56% by weight of a myriad of cells of odor counteractant oil scattered throughout and embedded in the binder, the odor counteractant oil being directly embedded in the binder without any intervening shell, and the cells having diameters between 2 μ and 300 82 , and the binder being impervious to migration of the odor counteractant therethrough.

21. The odor-counteracting medium of claim 20 in which the substrate is particles of pet litter.

22. The odor-counteracting medium of claim 21 in which the binder is gum tahla.

23. The odor-counteracting medium of claim 21 in which the cells of odor counteractant oil are droplets of fragrance oil having a viscosity of more than 1000 cps.

24. The odor-counteracting medium of claim 23 in which the thickening agent is dissolved in the fragrance oil in an amount not greater than about 10% of the weight of the fragrance oil.

25. The odor-counteracting medium of claim 24 in which the thickening agent is polyvinyl butyral.

26. The odor-counteracting medium of claim 23 in which the weight of the droplets of fragrance oil is between about 20% and 35% of the total weight of the dried film.

27. The macroemulsion of claim 15 comprising the following components in the following weight percentages:

| | |
|---|---|
| water | 40% and 75% |
| binder | 15% and 45% |
| fragrance oil | 4% and 25% |
| preservative | 0.1% and 5% |
| thickening agent | up to a maximum of about 10% |
| dye | up to a maximum of about 2% |
| surfactant | up to a maximum of about 2% |

* * * * *